US012714608B2

(12) United States Patent
Locke

(10) Patent No.: US 12,714,608 B2
(45) Date of Patent: Aug. 25, 2026

(54) LONG-TERM WEAR TISSUE INTERFACES FOR HIGH-CLOSURE FORCE NEGATIVE-PRESSURE THERAPY DRESSINGS

(71) Applicant: Solventum Intellectual Properties Company, Maplewood, MN (US)

(72) Inventor: Christopher Brian Locke, Bournemouth (GB)

(73) Assignee: Solventum Intellectual Properties Company, Maplewood, MN (US)

( * ) Notice: Subject to any disclaimer, the term of this patent is extended or adjusted under 35 U.S.C. 154(b) by 47 days.

(21) Appl. No.: 17/640,655

(22) PCT Filed: Sep. 2, 2020

(86) PCT No.: PCT/IB2020/058167

§ 371 (c)(1),
(2) Date: Mar. 4, 2022

(87) PCT Pub. No.: WO2021/044308

PCT Pub. Date: Mar. 11, 2021

(65) Prior Publication Data

US 2022/0355021 A1 Nov. 10, 2022

Related U.S. Application Data

(60) Provisional application No. 62/896,442, filed on Sep. 5, 2019.

(51) Int. Cl.
*A61F 13/05* (2024.01)
*A61L 15/20* (2006.01)
(Continued)

(52) U.S. Cl.
CPC .............. *A61F 13/05* (2024.01); *A61L 15/20* (2013.01); *A61L 15/325* (2013.01); *A61M 1/915* (2021.05); *A61M 1/916* (2021.05)

(58) Field of Classification Search
CPC .............. A61M 1/915; A61F 13/00068; A61F 13/00021
See application file for complete search history.

(56) References Cited

U.S. PATENT DOCUMENTS 1,355,846 A 10/1920 Rannells
2,547,758 A 4/1951 Keeling
(Continued)

FOREIGN PATENT DOCUMENTS

AU 550575 B2 3/1986
AU 745271 B2 3/2002
(Continued)

OTHER PUBLICATIONS

International Search Report and Written Opinion for Corresponding Application No. PCT/IB2020/058167 mailed Oct. 23, 2020.
(Continued)

*Primary Examiner* — Jacqueline F Stephens
*Assistant Examiner* — Nhu Q. Tran

(57) ABSTRACT

Dressings for treating a tissue site with negative pressure are disclosed, which may include a dressing having a manifold and a contact layer. In some embodiments, the manifold may comprise a plurality of holes, a first side, a second side, and a perimeter side between the first side and the second side. The contact layer may comprise collagen applied to the first side of the manifold and a perimeter side of the manifold. The plurality of holes of the manifold may include a center hole and a plurality of peripheral holes arranged around the center hole.

11 Claims, 7 Drawing Sheets

(51) Int. Cl.
*A61L 15/32* (2006.01)
*A61M 1/00* (2006.01)

(56) References Cited

U.S. PATENT DOCUMENTS

| | | | |
|---|---|---|---|
| 2,632,443 | A | 3/1953 | Lesher |
| 2,682,873 | A | 7/1954 | Evans et al. |
| 2,910,763 | A | 11/1959 | Lauterbach |
| 2,969,057 | A | 1/1961 | Simmons |
| 3,066,672 | A | 12/1962 | Crosby, Jr. et al. |
| 3,367,332 | A | 2/1968 | Groves |
| 3,520,300 | A | 7/1970 | Flower, Jr. |
| 3,568,675 | A | 3/1971 | Harvey |
| 3,648,692 | A | 3/1972 | Wheeler |
| 3,682,180 | A | 8/1972 | McFarlane |
| 3,826,254 | A | 7/1974 | Mellor |
| 4,080,970 | A | 3/1978 | Miller |
| 4,096,853 | A | 6/1978 | Weigand |
| 4,139,004 | A | 2/1979 | Gonzalez, Jr. |
| 4,165,748 | A | 8/1979 | Johnson |
| 4,184,510 | A | 1/1980 | Murry et al. |
| 4,233,969 | A | 11/1980 | Lock et al. |
| 4,245,630 | A | 1/1981 | Lloyd et al. |
| 4,256,109 | A | 3/1981 | Nichols |
| 4,261,363 | A | 4/1981 | Russo |
| 4,275,721 | A | 6/1981 | Olson |
| 4,284,079 | A | 8/1981 | Adair |
| 4,297,995 | A | 11/1981 | Golub |
| 4,333,468 | A | 6/1982 | Geist |
| 4,373,519 | A | 2/1983 | Errede et al. |
| 4,382,441 | A | 5/1983 | Svedman |
| 4,392,853 | A | 7/1983 | Muto |
| 4,392,858 | A | 7/1983 | George et al. |
| 4,419,097 | A | 12/1983 | Rowland |
| 4,465,485 | A | 8/1984 | Kashmer et al. |
| 4,475,909 | A | 10/1984 | Eisenberg |
| 4,480,638 | A | 11/1984 | Schmid |
| 4,525,166 | A | 6/1985 | Leclerc |
| 4,525,374 | A | 6/1985 | Vaillancourt |
| 4,540,412 | A | 9/1985 | Van Overloop |
| 4,543,100 | A | 9/1985 | Brodsky |
| 4,548,202 | A | 10/1985 | Duncan |
| 4,551,139 | A | 11/1985 | Plaas et al. |
| 4,569,348 | A | 2/1986 | Hasslinger |
| 4,605,399 | A | 8/1986 | Weston et al. |
| 4,608,041 | A | 8/1986 | Nielsen |
| 4,640,688 | A | 2/1987 | Hauser |
| 4,655,754 | A | 4/1987 | Richmond et al. |
| 4,664,662 | A | 5/1987 | Webster |
| 4,710,165 | A | 12/1987 | McNeil et al. |
| 4,733,659 | A | 3/1988 | Edenbaum et al. |
| 4,743,232 | A | 5/1988 | Kruger |
| 4,758,220 | A | 7/1988 | Sundblom et al. |
| 4,787,888 | A | 11/1988 | Fox |
| 4,826,494 | A | 5/1989 | Richmond et al. |
| 4,838,883 | A | 6/1989 | Matsuura |
| 4,840,187 | A | 6/1989 | Brazier |
| 4,863,449 | A | 9/1989 | Therriault et al. |
| 4,872,450 | A | 10/1989 | Austad |
| 4,878,901 | A | 11/1989 | Sachse |
| 4,897,081 | A | 1/1990 | Poirier et al. |
| 4,906,233 | A | 3/1990 | Moriuchi et al. |
| 4,906,240 | A | 3/1990 | Reed et al. |
| 4,919,654 | A | 4/1990 | Kalt |
| 4,941,882 | A | 7/1990 | Ward et al. |
| 4,953,565 | A | 9/1990 | Tachibana et al. |
| 4,969,880 | A | 11/1990 | Zamierowski |
| 4,985,019 | A | 1/1991 | Michelson |
| 5,037,397 | A | 8/1991 | Kalt et al. |
| 5,086,170 | A | 2/1992 | Luheshi et al. |
| 5,092,858 | A | 3/1992 | Benson et al. |
| 5,100,396 | A | 3/1992 | Zamierowski |
| 5,134,994 | A | 8/1992 | Say |
| 5,149,331 | A | 9/1992 | Ferdman et al. |
| 5,167,613 | A | 12/1992 | Karami et al. |
| 5,176,663 | A | 1/1993 | Svedman et al. |
| 5,215,522 | A | 6/1993 | Page et al. |
| 5,232,453 | A | 8/1993 | Plass et al. |
| 5,261,893 | A | 11/1993 | Zamierowski |
| 5,278,100 | A | 1/1994 | Doan et al. |
| 5,279,550 | A | 1/1994 | Habib et al. |
| 5,298,015 | A | 3/1994 | Komatsuzaki et al. |
| 5,342,376 | A | 8/1994 | Ruff |
| 5,344,415 | A | 9/1994 | DeBusk et al. |
| 5,358,494 | A | 10/1994 | Svedman |
| 5,437,622 | A | 8/1995 | Carion |
| 5,437,651 | A | 8/1995 | Todd et al. |
| 5,527,293 | A | 6/1996 | Zamierowski |
| 5,549,584 | A | 8/1996 | Gross |
| 5,556,375 | A | 9/1996 | Ewall |
| 5,607,388 | A | 3/1997 | Ewall |
| 5,636,643 | A | 6/1997 | Argenta et al. |
| 5,645,081 | A | 7/1997 | Argenta et al. |
| 6,071,267 | A | 6/2000 | Zamierowski |
| 6,135,116 | A | 10/2000 | Vogel et al. |
| 6,241,747 | B1 | 6/2001 | Ruff |
| 6,287,316 | B1 | 9/2001 | Agarwal et al. |
| 6,345,623 | B1 | 2/2002 | Heaton et al. |
| 6,488,643 | B1 | 12/2002 | Tumey et al. |
| 6,493,568 | B1 | 12/2002 | Bell et al. |
| 6,553,998 | B2 | 4/2003 | Heaton et al. |
| 6,814,079 | B2 | 11/2004 | Heaton et al. |
| 7,846,141 | B2 | 12/2010 | Weston |
| 8,062,273 | B2 | 11/2011 | Weston |
| 8,216,198 | B2 | 7/2012 | Heagle et al. |
| 8,251,979 | B2 | 8/2012 | Malhi |
| 8,257,327 | B2 | 9/2012 | Blott et al. |
| 8,398,614 | B2 | 3/2013 | Blott et al. |
| 8,449,509 | B2 | 5/2013 | Weston |
| 8,529,548 | B2 | 9/2013 | Blott et al. |
| 8,535,296 | B2 | 9/2013 | Blott et al. |
| 8,551,060 | B2 | 10/2013 | Schuessler et al. |
| 8,568,386 | B2 | 10/2013 | Malhi |
| 8,679,081 | B2 | 3/2014 | Heagle et al. |
| 8,834,451 | B2 | 9/2014 | Blott et al. |
| 8,926,592 | B2 | 1/2015 | Blott et al. |
| 9,017,302 | B2 | 4/2015 | Vitaris et al. |
| 9,198,801 | B2 | 12/2015 | Weston |
| 9,211,365 | B2 | 12/2015 | Weston |
| 9,289,542 | B2 | 3/2016 | Blott et al. |
| 2002/0077661 | A1 | 6/2002 | Saadat |
| 2002/0115951 | A1 | 8/2002 | Norstrem et al. |
| 2002/0120185 | A1 | 8/2002 | Johnson |
| 2002/0143286 | A1 | 10/2002 | Tumey |
| 2007/0185426 | A1 | 8/2007 | Ambrosio et al. |
| 2009/0177133 | A1* | 7/2009 | Kieswetter .............. A61P 17/02 602/75 |
| 2009/0312524 | A1* | 12/2009 | Lauritzen ............... A61K 38/17 530/356 |
| 2010/0069858 | A1* | 3/2010 | Olson ................... A61M 1/915 604/319 |
| 2010/0106106 | A1 | 4/2010 | Heaton et al. |
| 2010/0172889 | A1* | 7/2010 | Catchmark ............. A61P 43/00 424/94.1 |
| 2011/0070423 | A1* | 3/2011 | Jayakody ................ A61L 15/26 264/46.5 |
| 2011/0224630 | A1* | 9/2011 | Simmons ............. A61M 1/916 604/317 |
| 2012/0209227 | A1* | 8/2012 | Dunn ...................... A61M 1/84 604/319 |
| 2012/0245540 | A1 | 9/2012 | Zimnitsky et al. |
| 2014/0163491 | A1 | 6/2014 | Schuessler et al. |
| 2015/0080788 | A1 | 3/2015 | Blott et al. |
| 2015/0157758 | A1* | 6/2015 | Blucher .................. A61L 15/44 424/409 |
| 2016/0022885 | A1* | 1/2016 | Dunn .................... A61F 13/022 604/319 |
| 2018/0353339 | A1 | 12/2018 | Locke et al. |
| 2020/0170842 | A1* | 6/2020 | Locke ............... A61F 13/00068 |
| 2021/0077302 | A1* | 3/2021 | Carroll .................. A61L 15/425 |

(56) References Cited

U.S. PATENT DOCUMENTS

| | | | | |
|---|---|---|---|---|
| 2021/0196310 | A1* | 7/2021 | Moore | A61B 17/320758 |
| 2021/0205142 | A1* | 7/2021 | Rice | A61F 13/00068 |

FOREIGN PATENT DOCUMENTS

| | | | | |
|---|---|---|---|---|
| AU | 755496 | B2 | 12/2002 | |
| CA | 2005436 | A1 | 6/1990 | |
| DE | 26 40 413 | A1 | 3/1978 | |
| DE | 43 06 478 | A1 | 9/1994 | |
| DE | 29 504 378 | U1 | 9/1995 | |
| EP | 0100148 | A1 | 2/1984 | |
| EP | 0117632 | A2 | 9/1984 | |
| EP | 0161865 | A2 | 11/1985 | |
| EP | 0358302 | A2 | 3/1990 | |
| EP | 1018967 | A1 | 7/2000 | |
| EP | 3139877 | B1 * | 7/2018 | A61F 13/00008 |
| GB | 692578 | A | 6/1953 | |
| GB | 2195255 | A | 4/1988 | |
| GB | 2 197 789 | A | 6/1988 | |
| GB | 2 220 357 | A | 1/1990 | |
| GB | 2 235 877 | A | 3/1991 | |
| GB | 2 329 127 | A | 3/1999 | |
| GB | 2 333 965 | A | 8/1999 | |
| JP | 4129536 | B2 | 8/2008 | |
| SG | 71559 | | 4/2002 | |
| WO | 80/02182 | A1 | 10/1980 | |
| WO | 87/04626 | A1 | 8/1987 | |
| WO | 90/010424 | A1 | 9/1990 | |
| WO | 93/009727 | A1 | 5/1993 | |
| WO | 94/20041 | A1 | 9/1994 | |
| WO | 96/05873 | A1 | 2/1996 | |
| WO | 97/18007 | A1 | 5/1997 | |
| WO | 99/13793 | A1 | 3/1999 | |
| WO | 2019027731 | A1 | 2/2019 | |
| WO | 2020046443 | A1 | 3/2020 | |

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96.

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164.

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

(56) References Cited

OTHER PUBLICATIONS

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians; Jul. 2007.

* cited by examiner

LONG-TERM WEAR TISSUE INTERFACES FOR HIGH-CLOSURE FORCE NEGATIVE-PRESSURE THERAPY DRESSINGS

CROSS-REFERENCE TO RELATED APPLICATIONS

This application claims the benefit of priority to U.S. Provisional Application No. 62/896,442, filed on Sep. 5, 2019, which is incorporated herein by reference in its entirety.

TECHNICAL FIELD

The invention set forth in the appended claims relates generally to tissue treatment systems and more particularly, but without limitation, to dressing materials that may be worn for extended time periods for use with negative-pressure therapy.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," "vacuum-assisted closure," and "topical negative-pressure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

While the clinical benefits of negative-pressure therapy are widely known, improvements to therapy systems, components, and processes may benefit healthcare providers and patients.

BRIEF SUMMARY

New and useful systems, apparatuses, and methods for treating tissue in a negative-pressure therapy environment are set forth in the appended claims. Illustrative embodiments are also provided to enable a person skilled in the art to make and use the claimed subject matter.

For example, in some embodiments, an apparatus may comprise tissue dressing materials configured for lateral collapse and longer residency. In some examples, the materials may comprise a closure foam with biologically-active and degradable surfaces, which can prevent tissue ingrowth. Dressing materials may include a foam-based tissue interface that is coated or partially enclosed on multiple surfaces with a collagen-based material. The collagen-based material may prevent healing tissue from growing into the foam-based tissue interface materials, thereby allowing the tissue interface materials to remain in contact with the tissue site for longer periods of time. The tissue interface materials may be configured specifically for use in abdominal tissue sites.

In some embodiments, the closure foam may have through-holes configured to collapse laterally. The collagen may be provided as a fenestrated film or foam, and may be coated around the sides and lower surface of the closure foam, which is intended to be placed in contact with tissue. Additionally, the film or foam may cover or extend over the through-holes to reduce or prevent blister formation adjacent to the through-holes.

More generally, some embodiments of a dressing for treating a tissue site with negative pressure may include a manifold and a contact layer. The manifold may comprise a plurality of holes, a first side, a second side, and a perimeter side between the first side and the second side. The contact layer may comprise collagen applied to the first side of the manifold and the perimeter side of the manifold. In some embodiments, the contact layer may be in the form of a foam or a film. The contact layer may comprise perforations. Additionally, the dressing may include a glycerol coating disposed on the manifold between the first side of the manifold and the contact layer and between the perimeter side of the manifold and the contact layer. In some embodiments, the plurality of holes of the manifold may include a center hole and a plurality of peripheral holes arranged in a pattern around the center hole.

In some additional embodiments, a system for treating a tissue site may include a dressing comprising a manifold and a contact layer, a filler, a cover, and a negative-pressure source. The manifold may comprise a plurality of holes, a first side, a second side, and a perimeter side between the first side and the second side. The contact layer may comprise collagen applied to the first side of the manifold and the perimeter side of the manifold. The filler may be disposed adjacent to a central portion of the second side of the manifold. The cover may be disposed above the filler and configured to form a seal with the tissue site. The negative-pressure source may be fluidly coupled to the dressing.

In yet additional embodiments, a dressing for treating a tissue site may include a manifold pocket and a manifold. The manifold pocket may comprise a base layer and a border layer. The base layer may have a first side, a second side, and a perimeter edge. The border layer may be disposed around the perimeter edge of the base layer and may extend upwards from the second side of the base layer. The manifold may have a first side and a second side, and may be positioned within the manifold pocket. The manifold may be positioned within the manifold pocket such that the first side of the manifold is adjacent to the second side of the base layer, and the border layer of the manifold pocket is in contact with a perimeter surface of the manifold. The manifold pocket may comprise collagen, and in some instances may be in the form of a collagen foam or a collagen film. The manifold pocket may include perforations. The manifold may include a center hole and a plurality of peripheral holes arranged around the center hole.

In further embodiments, a method of configuring a dressing to be applied to a tissue site may include forming a pocket comprising collagen and disposing a manifold within the pocket. The pocket may include a base layer and a border layer forming a central cavity. The manifold may be disposed within the central cavity of the pocket. The method may further include removing the manifold from the central cavity of the pocket and disposing a replacement manifold within the central cavity of the pocket. In some embodiments, the method may further include reducing the size of the dressing by making a first cut and a second cut through a portion of the pocket and a portion of the manifold, removing a segment of the pocket and a segment of the manifold between the first cut and the second cut, and joining remaining portions of the pocket and the manifold adjacent to the first cut and the second cut to each other.

In still additional embodiments, a method of treating a compartmented wound site may include opening the compartmented wound site to form an open cavity, deploying a dressing within the compartmented wound site, connecting a negative-pressure connector subsystem to the dressing, deploying a cover to form a fluid seal over the open cavity, coupling the negative-pressure connector subsystem to a negative-pressure source, and activating the negative-pressure source. The dressing may include a manifold comprising a plurality of holes and a contact layer comprising collagen. The manifold may include a first side, a second side, and a perimeter side between the first side and the second side, and the contact layer may be applied to the first side of the manifold and the perimeter side of the manifold. In some instances, the compartmented wound site may be a peritoneal or abdominal cavity.

Objectives, advantages, and a preferred mode of making and using the claimed subject matter may be understood best by reference to the accompanying drawings in conjunction with the following detailed description of illustrative embodiments.

DESCRIPTION OF EXAMPLE EMBODIMENTS

The following description of example embodiments provides information that enables a person skilled in the art to make and use the subject matter set forth in the appended claims, but it may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

Figure 1:
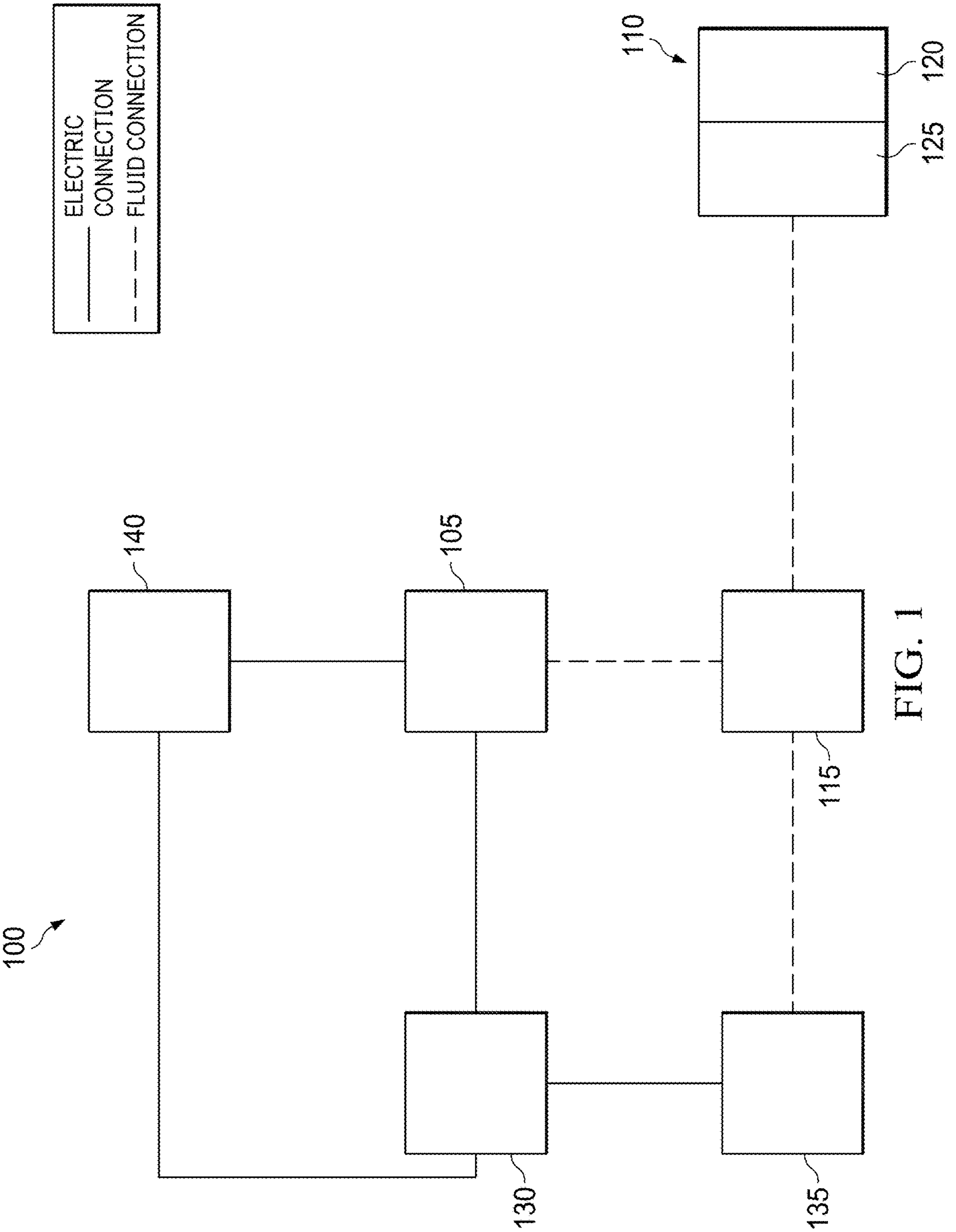
FIG. 1 is a functional block diagram of an example embodiment of a therapy system that can provide negative-pressure treatment in accordance with this specification.

FIG. 1 is a simplified functional block diagram of an example embodiment of a therapy system 100 that can provide negative-pressure therapy to a tissue site in accordance with this specification.

The term "tissue site" in this context broadly refers to a wound, defect, or other treatment target located on or within tissue, including, but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of any tissue that are not necessarily wounded or defective, but are instead areas in which it may be desirable to add or promote the growth of additional tissue. For example, negative pressure may be applied to a tissue site to grow additional tissue that may be harvested and transplanted.

The therapy system 100 may include a source or supply of negative pressure, such as a negative-pressure source 105, and one or more distribution components. A distribution component is preferably detachable and may be disposable, reusable, or recyclable. A dressing, such as a dressing 110, and a fluid container, such as a container 115, are examples of distribution components that may be associated with some examples of the therapy system 100. As illustrated in the example of FIG. 1, the dressing 110 may comprise or consist essentially of a tissue interface 120, a cover 125, or both in some embodiments.

A fluid conductor is another illustrative example of a distribution component. A "fluid conductor," in this context, broadly includes a tube, pipe, hose, conduit, or other structure with one or more lumina or open pathways adapted to convey a fluid between two ends. Typically, a tube is an elongated, cylindrical structure with some flexibility, but the geometry and rigidity may vary. Moreover, some fluid conductors may be molded into or otherwise integrally combined with other components. Distribution components may also include or comprise interfaces or fluid ports to facilitate coupling and de-coupling other components. In some embodiments, for example, a dressing interface may facilitate coupling a fluid conductor to the dressing 110. For example, such a dressing interface may be a SENSA-T.R.A.C.™ Pad available from Kinetic Concepts, Inc. of San Antonio, Texas.

The therapy system 100 may also include a regulator or controller, such as a controller 130. Additionally, the therapy system 100 may include sensors to measure operating parameters and provide feedback signals to the controller 130 indicative of the operating parameters. As illustrated in FIG. 1, for example, the therapy system 100 may include a first sensor 135 and a second sensor 140 coupled to the controller 130.

Some components of the therapy system 100 may be housed within or used in conjunction with other components, such as sensors, processing units, alarm indicators, memory, databases, software, display devices, or user interfaces that further facilitate therapy. For example, in some embodiments, the negative-pressure source 105 may be combined with the controller 130 and other components into a therapy unit.

In general, components of the therapy system 100 may be coupled directly or indirectly. For example, the negative-pressure source 105 may be directly coupled to the container 115 and may be indirectly coupled to the dressing 110 through the container 115. Coupling may include fluid, mechanical, thermal, electrical, or chemical coupling (such as a chemical bond), or some combination of coupling in some contexts. For example, the negative-pressure source 105 may be electrically coupled to the controller 130 and may be fluidly coupled to one or more distribution components to provide a fluid path to a tissue site. In some embodiments, components may also be coupled by virtue of physical proximity, being integral to a single structure, or being formed from the same piece of material.

A negative-pressure supply, such as the negative-pressure source 105, may be a reservoir of air at a negative pressure or may be a manual or electrically-powered device, such as a vacuum pump, a suction pump, a wall suction port available at many healthcare facilities, or a micro-pump, for example. "Negative pressure" generally refers to a pressure less than a local ambient pressure, such as the ambient pressure in a local environment external to a sealed therapeutic environment. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. References to increases in negative pressure typically refer to a decrease in absolute pressure, while decreases in negative pressure typically refer to an increase in absolute pressure. While the amount and nature of negative pressure provided by the negative-pressure source 105 may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −50 mm Hg (−6.7 kPa) and −300 mm Hg (−39.9 kPa).

The container 115 is representative of a container, canister, pouch, or other storage component, which can be used to manage exudates and other fluids withdrawn from a tissue site. In many environments, a rigid container may be preferred or required for collecting, storing, and disposing of fluids. In other environments, fluids may be properly disposed of without rigid container storage, and a re-usable container could reduce waste and costs associated with negative-pressure therapy.

A controller, such as the controller 130, may be a microprocessor or computer programmed to operate one or more components of the therapy system 100, such as the negative-pressure source 105. In some embodiments, for example, the controller 130 may be a microcontroller, which generally comprises an integrated circuit containing a processor core and a memory programmed to directly or indirectly control one or more operating parameters of the therapy system 100. Operating parameters may include the power applied to the negative-pressure source 105, the pressure generated by the negative-pressure source 105, or the pressure distributed to the tissue interface 120, for example. The controller 130 is also preferably configured to receive one or more input signals, such as a feedback signal, and programmed to modify one or more operating parameters based on the input signals.

Sensors, such as the first sensor 135 and the second sensor 140, are generally known in the art as any apparatus operable to detect or measure a physical phenomenon or property, and generally provide a signal indicative of the phenomenon or property that is detected or measured. For example, the first sensor 135 and the second sensor 140 may be configured to measure one or more operating parameters of the therapy system 100. In some embodiments, the first sensor 135 may be a transducer configured to measure pressure in a pneumatic pathway and convert the measurement to a signal indicative of the pressure measured. In some embodiments, for example, the first sensor 135 may be a piezo-resistive strain gauge. The second sensor 140 may optionally measure operating parameters of the negative-pressure source 105, such as a voltage or current, in some embodiments. Preferably, the signals from the first sensor 135 and the second sensor 140 are suitable as an input signal to the controller 130, but some signal conditioning may be appropriate in some embodiments. For example, the signal may need to be filtered or amplified before it can be processed by the controller 130. Typically, the signal is an electrical signal, but may be represented in other forms, such as an optical signal.

The tissue interface 120 can be generally adapted to partially or fully contact a tissue site. The tissue interface 120 may take many forms, and may have many sizes, shapes, or thicknesses, depending on a variety of factors, such as the type of treatment being implemented or the nature and size of a tissue site. For example, the size and shape of the tissue interface 120 may be adapted to the contours of deep and irregular shaped tissue sites. Any or all of the surfaces of the tissue interface 120 may have an uneven, coarse, or jagged profile.

In some embodiments, the tissue interface 120 may comprise or consist essentially of a manifold. A manifold in this context may comprise or consist essentially of a means for collecting or distributing fluid across the tissue interface 120 under pressure. For example, a manifold may be adapted to receive negative pressure from a source and distribute negative pressure through multiple apertures across the tissue interface 120, which may have the effect of collecting fluid from across a tissue site and drawing the fluid toward the source. In some embodiments, the fluid path may be reversed or a secondary fluid path may be provided to facilitate delivering fluid across a tissue site.

In some illustrative embodiments, a manifold may comprise a plurality of pathways, which can be interconnected to improve distribution or collection of fluids. In some illustrative embodiments, a manifold may comprise or consist essentially of a porous material having interconnected fluid pathways. Examples of suitable porous material that can be adapted to form interconnected fluid pathways (e g , channels) may include cellular foam, including open-cell foam such as reticulated foam; porous tissue collections; and other porous material such as gauze or felted mat that generally include pores, edges, and/or walls. Liquids, gels, and other foams may also include or be cured to include apertures and fluid pathways. In some embodiments, a manifold may additionally or alternatively comprise projections that form interconnected fluid pathways. For example, a manifold may be molded to provide surface projections that define interconnected fluid pathways.

In some embodiments, the tissue interface 120 may comprise or consist essentially of reticulated foam having pore sizes and free volume that may vary according to needs of a prescribed therapy. For example, reticulated foam having a free volume of at least 90% may be suitable for many therapy applications, and foam having an average pore size in a range of 400-600 microns (40-50 pores per inch) may be particularly suitable for some types of therapy. The tensile strength of the tissue interface 120 may also vary according to needs of a prescribed therapy. The 25% compression load deflection of the tissue interface 120 may be at least 0.35 pounds per square inch, and the 65% compression load deflection may be at least 0.43 pounds per square inch. In some embodiments, the tensile strength of the tissue interface 120 may be at least 10 pounds per square inch. The tissue interface 120 may have a tear strength of at least 2.5 pounds per inch. In some embodiments, the tissue interface may be foam comprised of polyols such as polyester or polyether, isocyanate such as toluene diisocyanate, and polymerization modifiers such as amines and tin compounds. In some examples, the tissue interface 120 may be reticulated polyurethane foam such as found in GRANUFOAM™ dressing or V.A.C. VERAFLO™ dressing, both available from Kinetic Concepts, Inc. of San Antonio, Texas.

The thickness of the tissue interface 120 may also vary according to needs of a prescribed therapy. For example, the thickness of the tissue interface may be decreased to reduce tension on peripheral tissue. The thickness of the tissue interface 120 can also affect the conformability of the tissue interface 120. In some embodiments, a thickness in a range of about 5 millimeters to 10 millimeters may be suitable.

The tissue interface 120 may be either hydrophobic or hydrophilic. In an example in which the tissue interface 120 may be hydrophilic, the tissue interface 120 may also wick fluid away from a tissue site, while continuing to distribute negative pressure to the tissue site. The wicking properties of the tissue interface 120 may draw fluid away from a tissue site by capillary flow or other wicking mechanisms. An example of a hydrophilic material that may be suitable is a polyvinyl alcohol, open-cell foam such as V.A.C. WHITEFOAM™ dressing available from Kinetic Concepts, Inc. of San Antonio, Texas. Other hydrophilic foams may include those made from polyether. Other foams that may exhibit hydrophilic characteristics include hydrophobic foams that have been treated or coated to provide hydrophilicity.

In some embodiments, the tissue interface 120 may be constructed from bioresorbable materials. Suitable bioresorbable materials may include, without limitation, a polymeric blend of polylactic acid (PLA) and polyglycolic acid (PGA). The polymeric blend may also include, without limitation, polycarbonates, polyfumarates, and capralactones. The tissue interface 120 may further serve as a scaffold for new cell-growth, or a scaffold material may be used in conjunction with the tissue interface 120 to promote cell-growth. A scaffold is generally a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

In some embodiments, the cover 125 may provide a bacterial barrier and protection from physical trauma. The cover 125 may also be constructed from a material that can reduce evaporative losses and provide a fluid seal between two components or two environments, such as between a therapeutic environment and a local external environment. The cover 125 may comprise or consist of, for example, an elastomeric film or membrane that can provide a seal adequate to maintain a negative pressure at a tissue site for a given negative-pressure source. The cover 125 may have a high moisture-vapor transmission rate (MVTR) in some applications. For example, the MVTR may be at least 250 grams per square meter per twenty-four hours in some embodiments, measured using an upright cup technique according to ASTM E96/E96M Upright Cup Method at 38° C. and 10% relative humidity (RH). In some embodiments, an MVTR up to 5,000 grams per square meter per twenty-four hours may provide effective breathability and mechanical properties.

In some example embodiments, the cover 125 may be a polymer drape, such as a polyurethane film, that is permeable to water vapor but impermeable to liquid. Such drapes typically have a thickness in the range of 25-50 microns. For permeable materials, the permeability generally should be low enough that a desired negative pressure may be maintained. The cover 125 may comprise, for example, one or more of the following materials: polyurethane (PU), such as hydrophilic polyurethane; cellulosics; hydrophilic polyamides; polyvinyl alcohol; polyvinyl pyrrolidone;

hydrophilic acrylics; silicones, such as hydrophilic silicone elastomers; natural rubbers; polyisoprene; styrene butadiene rubber; chloroprene rubber; polybutadiene; nitrile rubber; butyl rubber; ethylene propylene rubber; ethylene propylene diene monomer; chlorosulfonated polyethylene; polysulfide rubber; ethylene vinyl acetate (EVA); co-polyester; and polyether block polymide copolymers. Such materials are commercially available as, for example, Tegaderm® drape, commercially available from 3M Company, Minneapolis Minnesota; polyurethane (PU) drape, commercially available from Avery Dennison Corporation, Pasadena, California; polyether block polyamide copolymer (PEBAX), for example, from Arkema S.A., Colombes, France; and Inspire 2301 and Inpsire 2327 polyurethane films, commercially available from Expopack Advanced Coatings, Wrexham, United Kingdom. In some embodiments, the cover 125 may comprise INSPIRE 2301 having an MVTR (upright cup technique) of 2600 $g/m^2/24$ hours and a thickness of about 30 microns.

An attachment device may be used to attach the cover 125 to an attachment surface, such as undamaged epidermis, a gasket, or another cover. The attachment device may take many forms. For example, an attachment device may be a medically-acceptable, pressure-sensitive adhesive configured to bond the cover 125 to epidermis around a tissue site. In some embodiments, for example, some or all of the cover 125 may be coated with an adhesive, such as an acrylic adhesive, which may have a coating weight of about 25-65 grams per square meter (g.s.m.). Thicker adhesives, or combinations of adhesives, may be applied in some embodiments to improve the seal and reduce leaks. Other example embodiments of an attachment device may include a double-sided tape, paste, hydrocolloid, hydrogel, silicone gel, or organogel.

In operation, the tissue interface 120 may be placed within, over, on, or otherwise proximate to a tissue site. If the tissue site is a wound, for example, the tissue interface 120 may partially or completely fill the wound, or it may be placed over the wound. The cover 125 may be placed over the tissue interface 120 and sealed to an attachment surface near a tissue site. For example, the cover 125 may be sealed to undamaged epidermis peripheral to a tissue site. Thus, the dressing 110 can provide a sealed therapeutic environment proximate to a tissue site, substantially isolated from the external environment, and the negative-pressure source 105 can reduce pressure in the sealed therapeutic environment.

The fluid mechanics of using a negative-pressure source to reduce pressure in another component or location, such as within a sealed therapeutic environment, can be mathematically complex. However, the basic principles of fluid mechanics applicable to negative-pressure therapy are generally well-known to those skilled in the art, and the process of reducing pressure may be described illustratively herein as "delivering," "distributing," or "generating" negative pressure, for example.

In general, exudate and other fluid flow toward lower pressure along a fluid path. Thus, the term "downstream" typically implies something in a fluid path relatively closer to a source of negative pressure or further away from a source of positive pressure. Conversely, the term "upstream" implies something relatively further away from a source of negative pressure or closer to a source of positive pressure. Similarly, it may be convenient to describe certain features in terms of fluid "inlet" or "outlet" in such a frame of reference. This orientation is generally presumed for purposes of describing various features and components herein. However, the fluid path may also be reversed in some applications, such as by substituting a positive-pressure source for a negative-pressure source, and this descriptive convention should not be construed as a limiting convention.

Negative pressure applied across the tissue site through the tissue interface 120 in the sealed therapeutic environment can induce macro-strain and micro-strain in the tissue site. Negative pressure can also remove exudate and other fluid from a tissue site, which can be collected in container 115.

In some embodiments, the controller 130 may receive and process data from one or more sensors, such as the first sensor 135. The controller 130 may also control the operation of one or more components of the therapy system 100 to manage the pressure delivered to the tissue interface 120. In some embodiments, controller 130 may include an input for receiving a desired target pressure and may be programmed for processing data relating to the setting and inputting of the target pressure to be applied to the tissue interface 120. In some example embodiments, the target pressure may be a fixed pressure value set by an operator as the target negative pressure desired for therapy at a tissue site and then provided as input to the controller 130. The target pressure may vary from tissue site to tissue site based on the type of tissue forming a tissue site, the type of injury or wound (if any), the medical condition of the patient, and the preference of the attending physician. After selecting a desired target pressure, the controller 130 can operate the negative-pressure source 105 in one or more control modes based on the target pressure and may receive feedback from one or more sensors to maintain the target pressure at the tissue interface 120.

Figure 2:
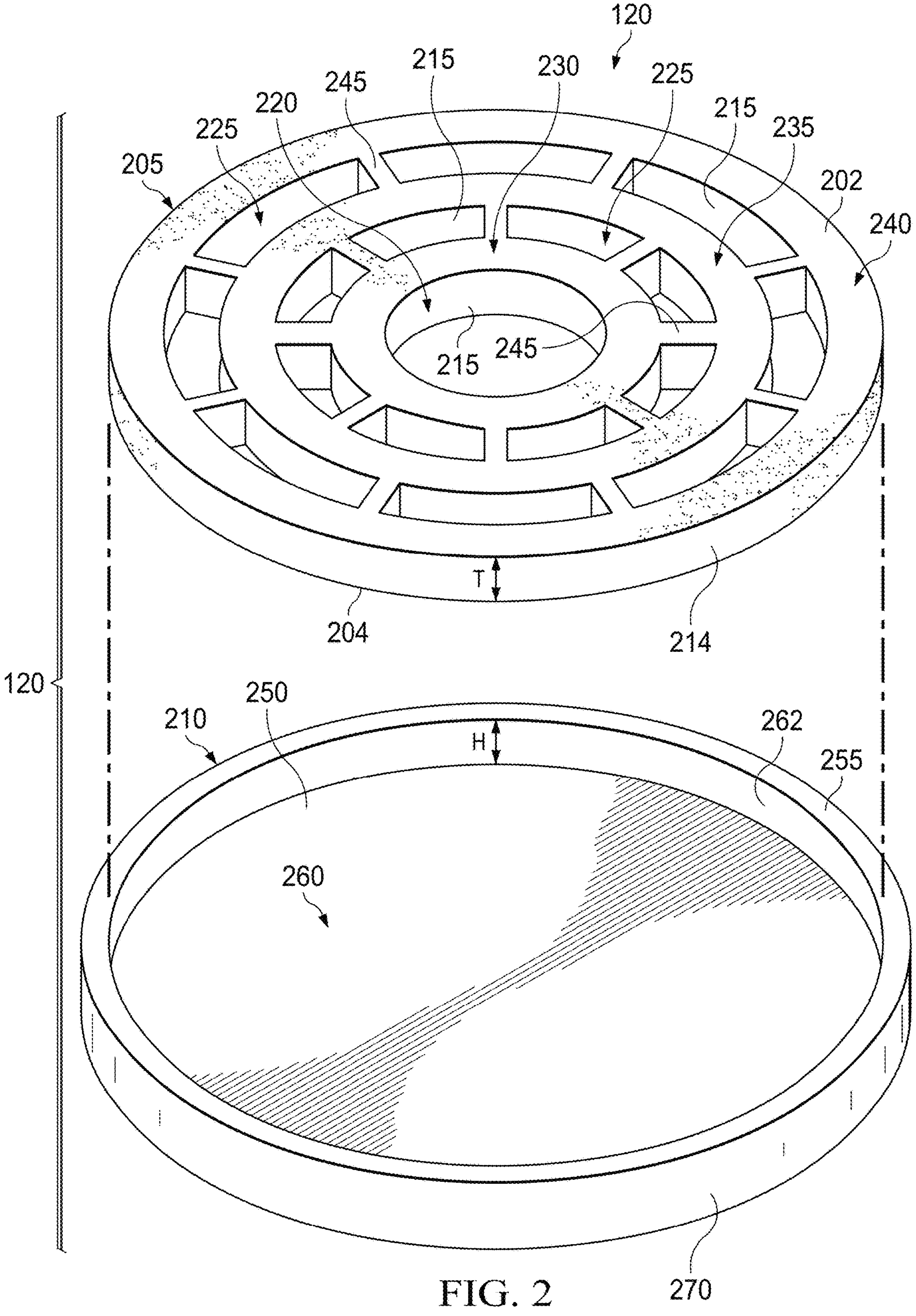
FIG. 2 is an assembly view of a tissue interface for use in the therapy system of FIG. 1 in accordance with this specification.

FIG. 2 is an assembly view of an example of the tissue interface 120 of FIG. 1, illustrating additional details that may be associated with some embodiments in which the tissue interface 120 comprises more than one layer. In the example of FIG. 2, the tissue interface 120 generally includes a first layer 205 and a second layer 210. The first layer 205 and the second layer 210 may be disposed adjacent to each other. The first layer 205 may be positioned on or within a portion of the second layer 210, and in some instances, the first layer 205 and the second layer 210 may be bonded to each other. As illustrated in FIG. 2, the first layer 205 and the second layer 210 may be geometrically similar. The tissue interface 120, including the individual first layer 205 and the second layer, 210 may be any number of different shapes, based on the particular anatomical needs of a tissue site. For example, the tissue interface 120 may have a circular, oval, square, rectangular, or other shape.

In some illustrative embodiments, the first layer 205 may comprise a plurality of pathways, which can be interconnected to improve distribution or collection of fluids. In some embodiments, the first layer 205 may comprise or consist essentially of a porous material having interconnected fluid pathways. For example, open-cell foam, reticulated foam, porous tissue collections, and other porous material such as gauze or felted mat generally include pores, edges, and/or walls adapted to form interconnected fluid channels. Liquids, gels, and other foams may also include or be cured to include apertures and fluid pathways. In some embodiments, the first layer 205 may additionally or alternatively comprise projections that form interconnected fluid pathways. For example, the first layer 205 may be molded to provide surface projections that define interconnected fluid pathways. Any or all of the surfaces of the first layer 205 may have an uneven, coarse, or jagged profile.

In some embodiments, the first layer 205 may comprise or consist essentially of a reticulated foam having pore sizes and free volume that may vary according to needs of a prescribed therapy. For example, a reticulated foam having a free volume of at least 90% may be suitable for many therapy applications, and a foam having an average pore size in a range of 400-600 microns (40-50 pores per inch) may be particularly suitable for some types of therapy. The tensile strength of the first layer 205 may also vary according to needs of a prescribed therapy. For example, the tensile strength of a foam may be increased for instillation of topical treatment solutions. The 25% compression load deflection of the first layer 205 may be at least 0.35 pounds per square inch, and the 65% compression load deflection may be at least 0.43 pounds per square inch. In some embodiments, the tensile strength of the first layer 205 may be at least 10 pounds per square inch. The first layer 205 may have a tear strength of at least 2.5 pounds per inch. In some embodiments, the first layer 205 may be a foam comprised of polyols such as polyester or polyether, isocyanate such as toluene diisocyanate, and polymerization modifiers such as amines and tin compounds. In one non-limiting example, the first layer 205 may be a reticulated polyurethane ether foam such as used in GRANUFOAM™ dressing or V.A.C. VERAFLO™ dressing, both available from KCI of San Antonio, Texas.

The first layer 205 may include either or both of hydrophobic and hydrophilic materials. In an example in which the first layer 205 may be hydrophilic, the first layer 205 may also wick fluid away from a tissue site, while continuing to distribute negative pressure to the tissue site. The wicking properties of the first layer 205 may draw fluid away from a tissue site by capillary flow or other wicking mechanisms. An example of a hydrophilic foam is a polyvinyl alcohol, open-cell foam such as V.A.C. WHITEFOAM™ Dressing available from Kinetic Concepts, Inc. of San Antonio, Texas. Other hydrophilic foams may include those made from polyether. Other foams that may exhibit hydrophilic characteristics include hydrophobic foams that have been treated or coated to provide hydrophilicity.

The first layer 205 of FIG. 2 generally has a first planar surface 202 and a second planar surface 204, which is generally parallel to the first planar surface 202. The thickness T of the first layer 205 between the first planar surface 202 and the second planar surface 204 may also vary according to needs of a prescribed therapy. For example, the thickness of the first layer 205 may be decreased to relieve stress on other layers and to reduce tension on peripheral tissue. The thickness of the first layer 205 can also affect the conformability of the first layer 205. In some embodiments, a thickness in a range of about 5 millimeters to 10 millimeters may be suitable. The first layer 205 may also have a peripheral surface 214 between the first planar surface 202 and the second planar surface 204.

The first layer 205 may comprise one or more apertures 215 that extend either partially or fully through the thickness of the first layer 205. As illustrated in FIG. 2, the apertures 215 may be through-holes in some examples. Additionally, the apertures 215 may be arranged in a variety of patterns. For example, FIG. 2 illustrates an exemplary pattern of apertures 215 that may be associated with some embodiments of the first layer 205. In the example of FIG. 2, the apertures 215 comprises a central aperture 220 and a plurality of peripheral apertures 225. The central aperture 220 and each of the plurality of peripheral apertures 225 may have a length ranging from about 10 mm to about 20 mm and a width ranging from about 5 mm to about 10 mm. The central aperture 220 and each of the plurality of peripheral apertures 225 may have sharp corners or may have a radius in each of the corners as desired. Where the central aperture 220 and each of the plurality of peripheral apertures 225 have a same width over the entire area of the first layer 2055, uniform collapse may be achieved, whereas differing widths can result in different levels of collapse over the area. For example, an apertures having a larger width can collapse more than an aperture having a thinner width. Further, the size of the apertures may be chosen based on the overall size of the first layer 205. For example, a smaller first layer 205 may have a larger number of thinner slots, while a larger first layer 205 may have a smaller number of wider slots.

As shown in FIG. 2, the plurality of peripheral apertures 225 may be arranged in a pattern of concentric rings, which may demarcate divisions between portions of the first layer 205, such as an inner portion 230, a first perimeter portion 235, and a second perimeter portion 240. As illustrated, the inner portion 230 may form a circular or elliptical cylinder around the central aperture 220. The first perimeter portion 235 may be concentric with the inner portion 230, and the second perimeter portion 240 may be concentric with both the inner portion 230 and the first perimeter portion 235. The first layer 205 may further include connecting segments 245, which extend between the inner portion 230 and the first perimeter portion 235 and between the first perimeter portion 235 and the second perimeter portion 240. In additional or alternative embodiments, the first layer 205 may include additional or fewer perimeter portions, depending on the particular size and/or shape desired for the first layer 205. In additional or alternative embodiments, suitable profiles of the first layer 205 may include interconnected concentric rings or arcs, or some combination of appendages, rings, and arcs, which may be coupled to or form a central body. In some examples, the connecting segments 245 may improve flexibility between the portions of the first layer 205.

The second layer 210 may comprise or consist of a material suited for being in longer-term contact with a tissue site. The second layer 210 may comprise a variety of materials, and in some embodiments, may comprise a biologically-derived polymer such as collagen, gelatin, collagen-like proteins, collagen-like peptides, or combinations of these materials. In some embodiments, the second layer 210 can include glycerol, which can make the material to some degree flexible and plastic when dry. The second layer 210 may be in the form of a foam or film, such as a collagen based foam or film.

In some embodiments, the second layer 210 may comprise a plurality of layers of freeze dried collagen. The plurality of layers of freeze dried collagen may be assembled when slightly wet.

In some alternative embodiments, the second layer 210 may additionally comprise cellulose or a cellulose derivative, such as oxidized regenerated cellulose (ORC), or chemically-modified cellulose.

In some embodiments, the second layer 210 may comprise a variety of different combinations or mixtures of materials. For example, some embodiments of the second layer 210 may comprise a combination of gelatin and collagen. Some additional embodiments of the second layer 210 may comprise a combination of collagen and ORC materials. For example, the second layer 210 may comprise a composite of approximately 50% collagen and 50% ORC, and in some preferred embodiments, the second layer 210 may comprise a composite of approximately 55% collagen and 45% ORC by weight. However, the proportions of each of the collagen and ORC may vary. For example, the second layer 210 may comprise a composite of collagen and ORC, with the amount of collagen ranging from 20% to 80% of the total weight of the second layer 210 and the amount of ORC ranging from 20% to 80% of the total weight of the second layer 210. In some embodiments, the second layer 210 may comprise or consist essentially of material found in PROMOGRAN™ Matrix Wound Dressing, commercially available from Kinetic Concepts, Inc. of San Antonio, Texas. In some embodiments, the second layer 210 may comprise collagen, ORC, and DSS. For example, the second layer 210 may comprise from about 50% to about 60% collagen and from about 40% to about 50% ORC by weight of the second layer 210, and from about 30 μg/ml to about 1,000 μg/ml DSS, by volume of the second layer 210. Additionally, in some, still more particular embodiments, the second layer 210 may comprise collagen, ORC, DSS, and PHMB. For example, the second layer 210 may comprise from about 50% to about 60% collagen and from about 40% to about 50% ORC, and from about 0.005% to about 0.025% PHMB, by weight of the second layer 210, and from about 30 μg/ml to about 1,000 μg/ml DSS by volume of the second layer 210.

The configuration of the second layer 210 may vary depending on the particular application of the tissue interface 120. For example, in some embodiments the second layer 210 may comprise or consist essentially of a base layer or bottom portion 250. The second layer 210 may further comprise a border portion 255, which may extend around the periphery or circumference of the bottom portion 250. In some embodiments, the border portion 255 may extend upwards from the bottom portion 250 around the entire periphery of the base portion 250, as illustrated FIG. 2, so as to form an inner volume or pocket 260 within the second layer 210. The border portion 255 may have an inner surface 262 having a height H that corresponds to the thickness T of the first layer 205.

In some embodiments, as illustrated in FIG. 2, the second layer 210 may have substantially a circular or oval shape that may generally correspond to the shape of the first layer 205. However, the second layer 210 may also comprise a variety of other shapes, depending on the desired shape of the first layer 205 and overall tissue interface 120.

In some embodiments, the second layer 210 does not include any perforations or slits, such that the second layer 210 is a solid manifolding foam of collagen which prevents blisters forming under the first layer 205 in open wounds.

The second layer 210 may also range in size and associated dimensions, depending on the particular configuration of the tissue interface 120. In some embodiments, the bottom portion 250 may have a thickness between approximately 2.0 mm and 5.0 mm. In some particular embodiments, the bottom portion 250 may have a thickness between approximately 2.5 mm and 4.5 mm. The material of the second layer 210 may allow for air to flow through the second layer 210 for effective communication of negative pressure within and through the tissue interface 120. In some embodiments, the second layer 210 has a density of between 0.012 $g/cm^3$ and 0.020 $g/cm^3$.

In some embodiments, the second layer 210 may also assist with reducing or preventing the presence of deleterious or infectious substances within the tissue interface 120 and at the tissue site. For example, the material of the second layer 210 may treat microbial agents that may be present in wound fluids and pose a risk to the tissue site. The second layer 210 may therefore provide an antimicrobial benefit to the tissue interface 120.

Figure 3:
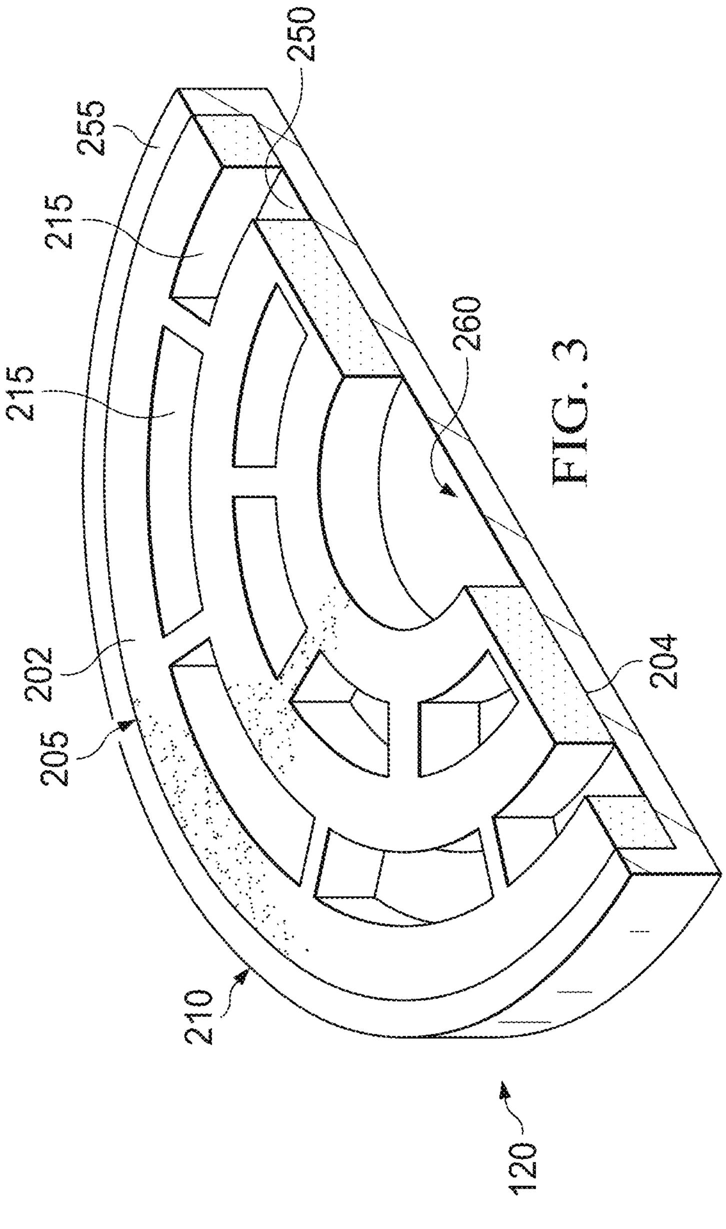
FIG. 3 is a cross-section view of the tissue interface of FIG. 2 for use in the therapy system of FIG. 1 in accordance with this specification.

FIG. 3 is a perspective cut-away view of the tissue interface 120 of FIG. 2, illustrating additional details that may be associated with some embodiments. For example, as shown in FIG. 3, the first layer 205 may be positioned or seated within the pocket 260 of the second layer 210 of the tissue interface 120 and can substantially occupy the pocket 260. In some instances, the dimensions of the first layer 205 may be such that the outer periphery of the first layer 205, such as the peripheral surface 214 (shown in FIG. 2) of the first layer 205 may be positioned in contact with the inner surface 262 (shown in FIG. 2) of the border portion 255 of the second layer 210. Assembled as illustrated in FIG. 3, the first planar surface 202 may form a first side of the tissue interface 120, and the second layer 210 may form a second side of the tissue interface 120. FIG. 3 also illustrates an example configuration in which the second layer 210 extends across or otherwise covers at least some of the apertures 215. In the example of FIG. 3, the base portion 250 covers the apertures 215.

As may also be understood from FIG. 3, the second layer 210 may be conformed or applied to the first layer 205 in a variety of ways. For example, the second layer 210 may be applied to the first layer 205 as a coating. For example, the second layer 210 may be applied as a coating around the second planar surface 213 and the peripheral surface 214 of the first layer 205 so as to form the border portion 255 and the bottom portion 250 of the second layer 210, respectively. In additional embodiments, rather than being coated onto the first layer 205 and then dried, the material of the second layer 210 may be cast and dried as a separate structure having the size and the shape within which the first layer 205 may fit. In some instances, the second layer 210 may be supplied as a cast shape and packaged separately from the first layer 205, therefore allowing a caregiver or provider to apply the second layer 210 and the first layer 205 as two separate steps.

Figure 4:
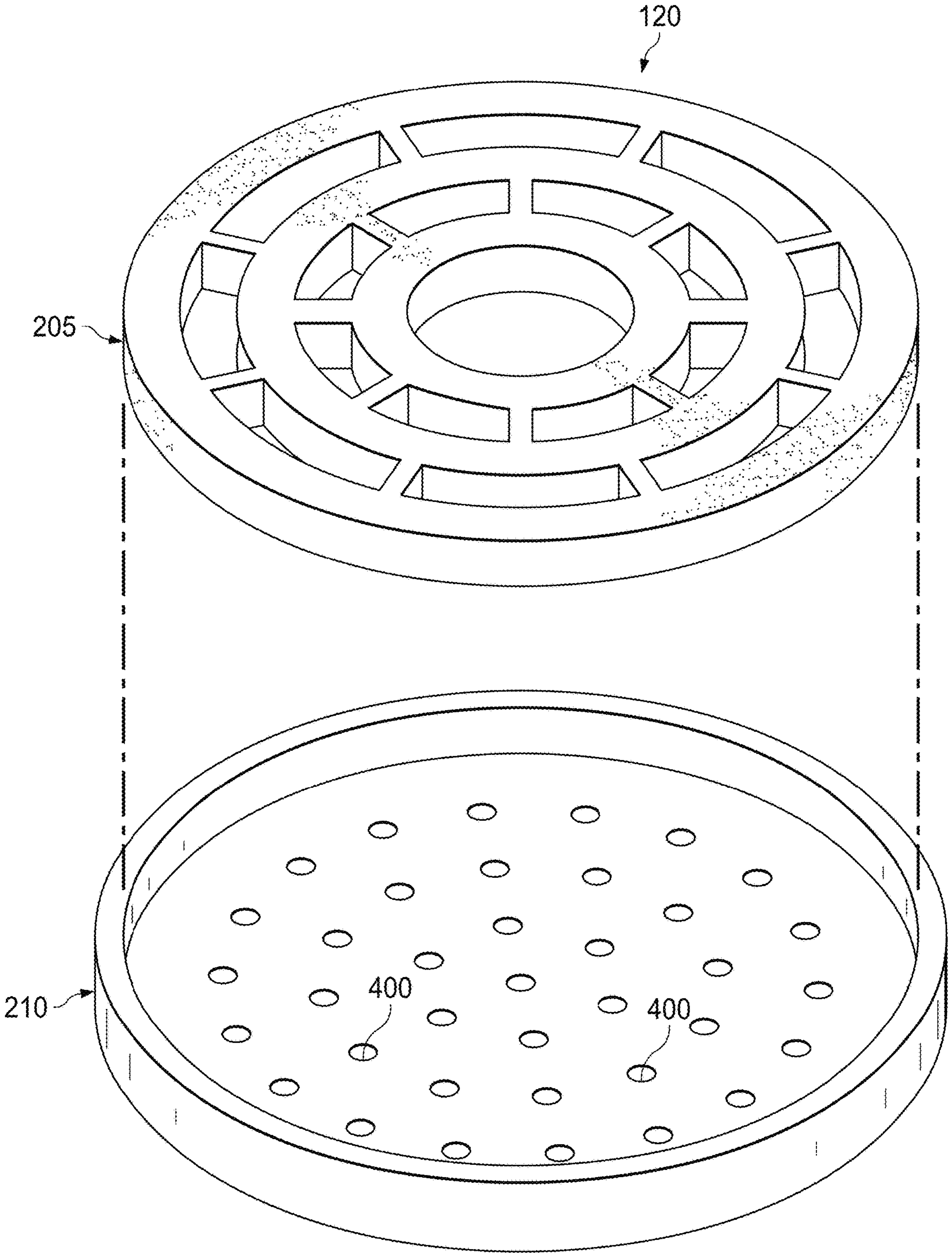
FIG. 4 is an assembly view of a tissue interface for use in the therapy system of FIG. 1 in accordance with this specification.

In another embodiment, as shown in FIG. 4, the second layer 210 may include one or more apertures or holes 400 in the base portion 250. In some embodiments, each of the apertures or holes 400 may be circular and may have a diameter of between 1 mm and 10 mm. In some other instances, each of the apertures or holes 400 may be in the form of a slot having a length between 1 mm and 10 mm and a width between 1 mm and 5 mm. For example, each of the openings may have a polygonal shape or square shape having sides with a length between 1 mm and 10 mm. In some embodiments, the apertures or holes 400 may be in the form of circular openings and slots.

Figure 5:
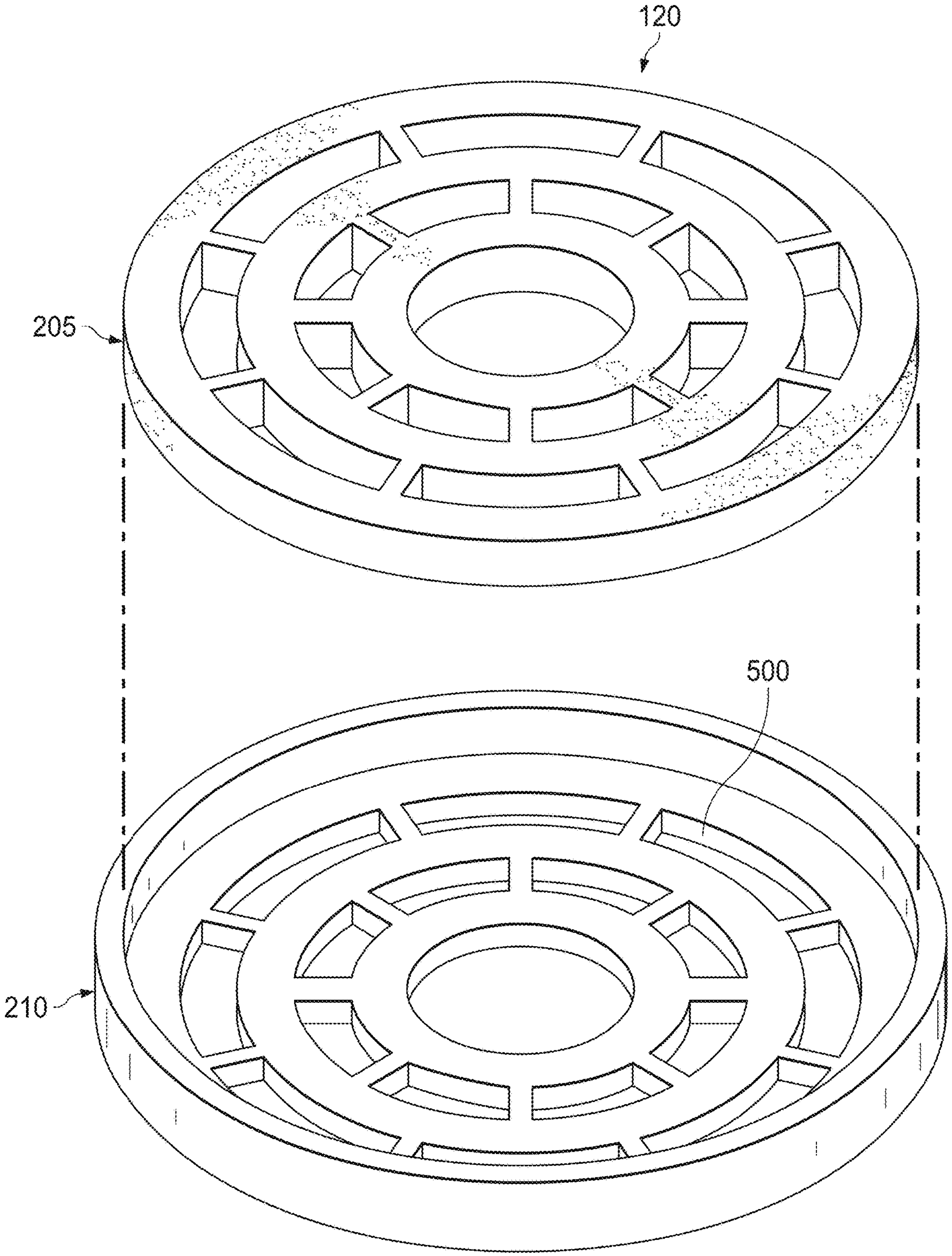
FIG. 5 is an assembly view of a tissue interface for use in the therapy system of FIG. 1 in accordance with this specification.

In another embodiment, as shown in FIG. 5, the second layer 210 may comprise a plurality of openings 500, which in some instances, may correspond to the one or more apertures 215 of the first layer 205. The size and shape of the openings 500 of the second layer 210 may correspond or be analogous to the size and shape of the one or more apertures 215 of the first layer. Regardless, the size and shape of the one or more openings 500 of the second layer 210 may vary.

Figure 6A:
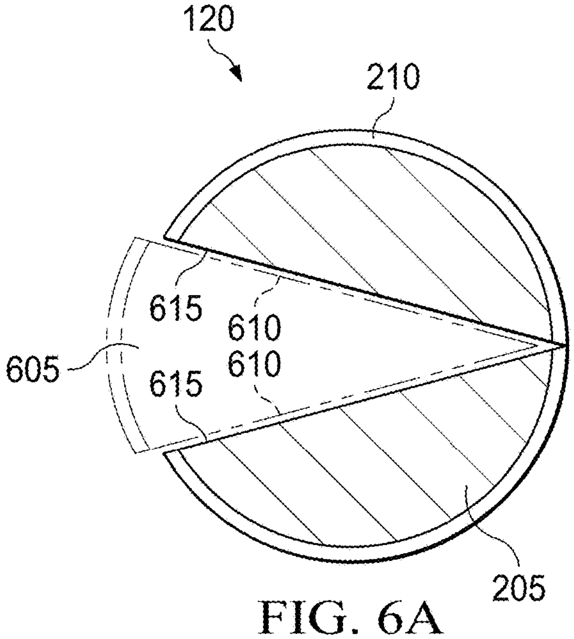
FIGS. 6A, 6B, and 6C are illustrations of a method of sizing the tissue interface for use in the therapy system of FIG. 1 in accordance with this specification.
Figure 6B:
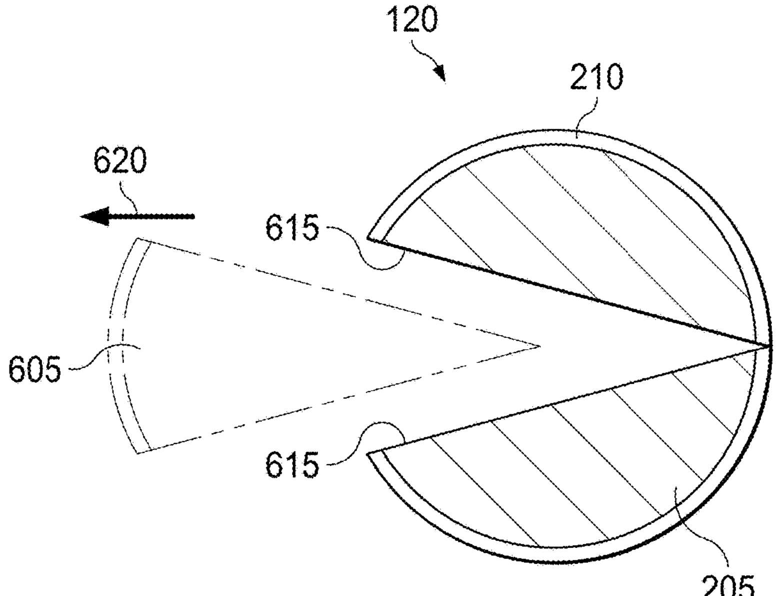
Figure 6C:
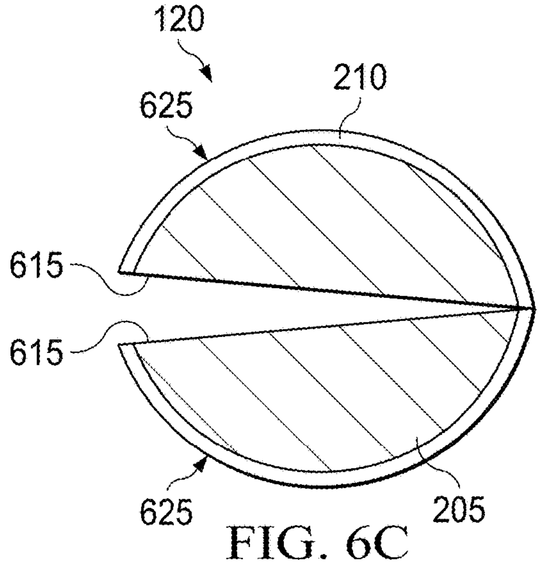

FIGS. 6A-6C collectively illustrate a method for sizing and/or resizing the tissue interface 120, according to some illustrative embodiments. Although the individual layers of the tissue interface 120 may be separately sized prior to assembly, it may be easier to size the tissue interface 120 once the individual layers have been assembled with and/or adhered to each other. As shown in FIGS. 6A-6C, the individual layers of the tissue interface 120 may be simultaneously sized so as to reduce duplicative efforts as well as to ensure that the sizes of the individual layers correspond appropriately to each other once they have been adjusted.

Referring now primarily to FIG. 6A, the first layer 205 and the second layer 210 may already be assembled or pre-assembled so as to form the tissue interface 120. For example, in some instances, the tissue interface 120 may be provided in a standard circular or cylindrical size having the second layer 210 coated on the first layer 205, and it may be desirable to reduce the overall size of the tissue interface 120. As illustrated in FIG. 6A, in order to reduce the size of the tissue interface 120, a portion or segment 605 may be removed.

As shown, in some embodiments, in order to make such a size reduction for a circular or cylindrically-shaped tissue interface 120, a segment 605 may be created out of and then removed from the tissue interface 120. As illustrated in the example of FIG. 6A-6C, the segment 605 may have a triangular or wedge shape. In order to remove segment 605, one or more cuts 610 through a thickness of the tissue interface 120 may be required, depending on the specific embodiment. For example, FIG. 6A shows that the cuts 610 include two linear cuts formed across and through the first layer 205 and the second layer 210 of the tissue interface 120 in order to create the segment 605 in a region between the cuts 610. Creating the cuts 610 across the tissue interface 120 may create one or more exposed surfaces, such as interior surfaces 615, through the thicknesses of both the first layer 205 and the second layer 210 of the tissue interface 120. In some embodiments, the tissue interface 120 may be perforated radially, such that the first layer 205 and the second layer 210 can be sectioned without the need for tools.

Referring now to FIG. 6B, it can be seen how once the cuts 610 across the tissue interface 120 have been made, the segment 605 may be completely removed. The interior surfaces 615 may then remain exposed to one another. The cuts 610 and associated exposed interior surfaces 615 may extend substantially across the tissue interface 610, however may not extend completely across the diameter or width of the tissue interface 120, so as to avoid dividing the tissue interface 120 into multiple portions that may become separated from each other. Thus, as shown in FIGS. 6A and 6B, the cuts 610 and associated interior surfaces 615 may not extend through at least a portion of the border portion 255 of the second layer 210 opposite to widest point of the opening of the tissue interface 120 formed by the cuts 610. In other embodiments, perhaps where the tissue interface 120 comprises a shape other than circular or cylindrical, the cuts 610 may only extend across a portion of a width or other dimension of the tissue interface 120.

Following the removal of the segment 605, the sizing of the tissue interface 120 may be completed, as shown in FIG. 6C. For example, once the segment 605 has been fully removed from the remainder of the tissue interface 120, the exposed interior surfaces 615 may be brought or pushed together, according to direction 625, to be in contact with each other in order to close the opening or void created by removal of the segment 605. In order to ensure that the interior surfaces 615 may remain in contact with each other, an attachment mechanism such as an adhesive may be applied to one or more of the interior surfaces 615, however depending on the overall structure of the tissue interface 120 and/or dressing 110, such attachment mechanisms may not be needed.

Figure 7:
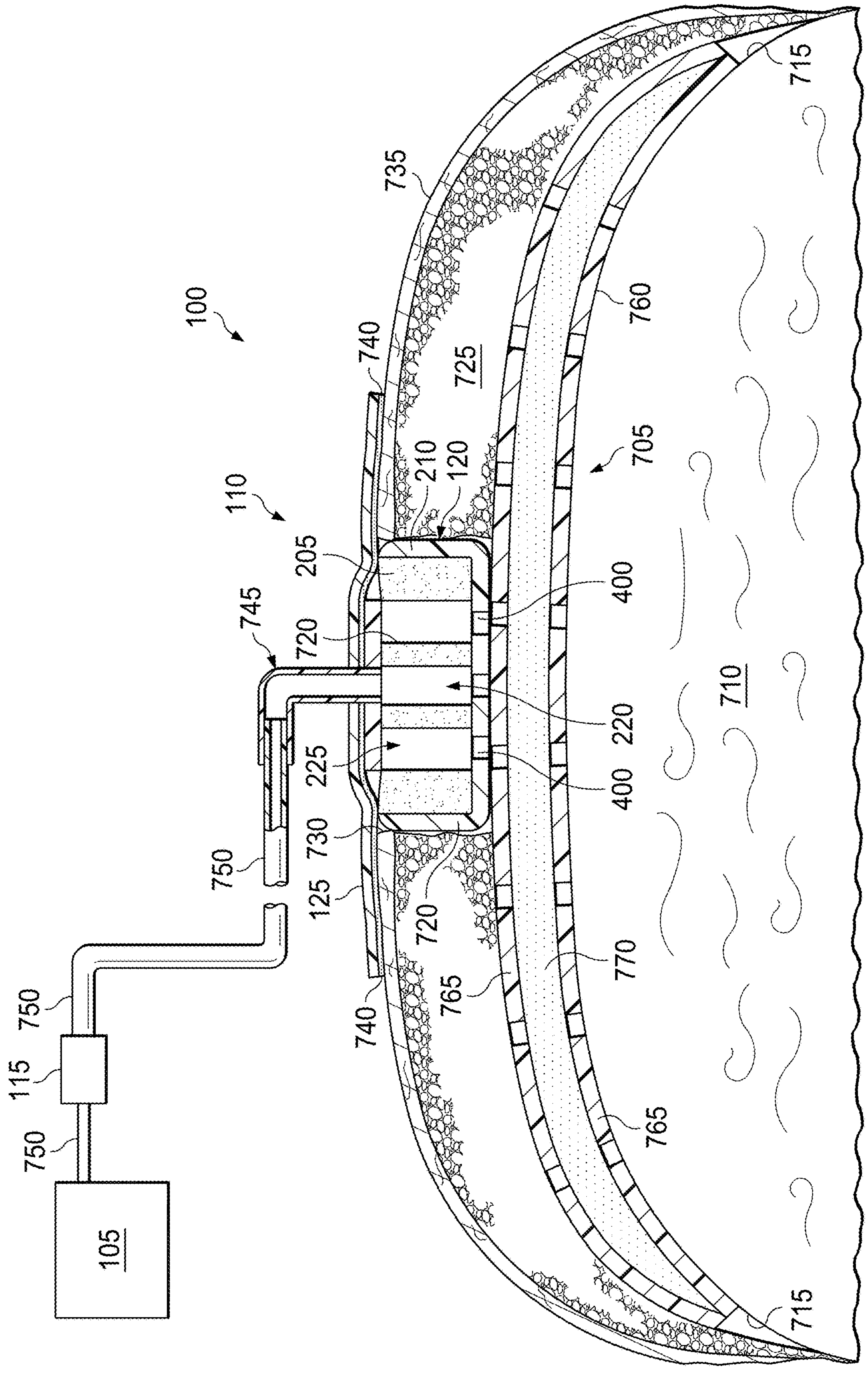
FIG. 7 is a cross-sectional view of the therapy system illustrating additional details that may be associated with an example embodiment of therapy system of FIG. 1.

FIG. 7 is a schematic view of an example of a therapy system 100 in which the tissue interface 120 is applied to a tissue site that comprises an abdominal cavity 705. As shown, the tissue interface 120 includes the first layer 205 and the second layer 210, which may be sufficiently flexible to conform to a tissue site, and which may act as a closure manifold 720. In some embodiments, the tissue interface 120 also includes a viscera contact layer 760. The viscera contact layer 760 includes a first viscera contact layer 765 and a second viscera contact layer 770, which are coupled to form the viscera contact layer 760.

For example, the first layer 205 and the second layer 210 of the closure manifold 720 FIG. 7 can be inserted into the abdominal cavity 705 along with the viscera contact layer 760. In the example of FIG. 7, the tissue interface 120 is supported by abdominal contents 710. The tissue interface 120 may be positioned within the abdominal cavity 705 such that edges of the viscera contact layer 760 of the tissue interface 120 may extend into the paracolic gutter 715. While the exemplary embodiment in FIG. 7 is applied to the abdomen, it will be appreciated that the tissue interface 120 and the associated technique can be applied to other open wounds where closure of swollen and traumatized tissues by re-approximation are desired.

In the example of FIG. 7, the dressing 110 includes the closure manifold 720, which is configured to deliver negative pressure through the abdominal wall 725. For example, the closure manifold 720 may be inserted through an opening 730 in the abdominal wall 725 and disposed adjacent to the viscera contact layer 760 in fluid communication with the first viscera contact layer 765. As illustrated in FIG. 7, the cover 125 may be placed over the opening 730 and sealed to epidermis 735 around the opening 730. For example, an attachment device such as an adhesive layer 740 may be disposed around a perimeter of the cover 125 to secure the cover 125 to the epidermis 735.

FIG. 7 further illustrates an example of a dressing interface 745 fluidly coupling the dressing 110 to a fluid conductor 750. The dressing interface 745 may be, as one example, a port or connector, which permits the passage of fluid from the closure manifold 720 to the fluid conductor 750 and vice versa. The dressing interface 745 of FIG. 7 comprises an elbow connector. Fluid collected from the abdominal cavity 705 may enter the fluid conductor 750 via the dressing interface 745. In other examples, the therapy system 100 may omit the dressing interface 745, and the fluid conductor 750 may be inserted directly through the cover 125 and into the closure manifold 720. In some examples, the fluid conductor 750 may have more than one lumen. For example, the fluid conductor 750 may have one lumen for negative pressure and liquid transport and one or more lumens for communicating pressure to a pressure sensor.

A negative pressure may be applied to the tissue interface 120, and more specifically, the first layer 205 and the second layer 210 of the closure manifold 720. In some embodiments, each of the first layer 205 and the second layer 210 may function as a manifold. For example, the perforations 400 in the second layer 210 may allow fluid to be collected or distributed through and across the second layer 210 of the tissue interface 120 under negative pressure. Furthermore, the apertures 215 of the first layer 205 may allow fluid to be transported through the first layer 205 under negative pressure. Fluid can move directly or indirectly through the first layer 205 and the second layer 210 of the tissue interface 120 towards the negative-pressure source 105. As negative pressure is applied to the tissue interface 120, the first layer 205 may contract. For example, the apertures 215 may collapse laterally, which can result in the tissue interface 120 applying a closure force to the abdominal wall 725. The second layer 210 may provide an interface between the first layer 205 and the abdominal contents 710, as well as prevent ingrowth of tissue into the first layer 205.

The systems, apparatuses, and methods described herein may provide significant advantages. For example, tissue interface 120 can be used in an open cavity for lateral collapse and can substantially reduce or prevent tissue ingrowth. Further, the second layer 210 can be configured such that collapse of the material in the cavity is not compromised, and the second layer 210 can provide a substantially flat or smooth contact surface. In some examples, the second layer 210 can substantially reduce or prevent blister formation. The tissue interface 120 can include a hydrophilic collagen material that is designed to hydrate quickly and remain structural for at least 3 to 7 days. Additionally, or alternatively, the tissue interface 120 may comprise a pocket, which can allow a manifold layer to be removed without disrupting the rest of the tissue interface 120. For example, the first layer 205 may be pre-coated with glycerol to aid in removal of the first layer 205 from the second layer 210. In some embodiments, the second layer 210 may not be coated on the first layer 205, but may be cast and dried into a desired shaped. Thus, the second layer 210 may be supplied as a cast shape and packaged separately from the first layer 205 allowing the first layer 205 and the second layer 210 to be applied separately. The second layer 205 may include or be formed of collagen in some examples, and once hydrated, the collagen can provide a low surface friction and assist with tissue, bone, and/or bowel movement, and allows the appropriate contraction of the overall structure.

While shown in a few illustrative embodiments, a person having ordinary skill in the art will recognize that the systems, apparatuses, and methods described herein are susceptible to various changes and modifications that fall within the scope of the appended claims. Moreover, descriptions of various alternatives using terms such as "or" do not require mutual exclusivity unless clearly required by the context, and the indefinite articles "a" or "an" do not limit the subject to a single instance unless clearly required by the context. Components may be also be combined, separated, or eliminated in various configurations for purposes of sale, manufacture, assembly, or use. For example, in some configurations the dressing 110, the container 115, or both may be separated from other components for manufacture or sale. In other example configurations, the controller 130 may also be manufactured, configured, assembled, or sold independently of other components.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described in the context of some embodiments may also be omitted, combined, or replaced by alternative features serving the same, equivalent, or similar purpose without departing from the scope of the invention defined by the appended claims.

What is claimed is:

1. A dressing for treating a tissue site with negative pressure, comprising:

a manifold comprising a first side, a second side, a perimeter side, and a plurality of through-holes extending from the first side to the second side; and a contact layer applied to the first side of the manifold, the contact layer comprising collagen and having:

a base layer; and a border portion extending away from the base layer around the periphery of the base layer, the border portion having a surface configured to contact the perimeter side of the manifold.

2. The dressing of claim 1, wherein the collagen is a collagen foam having open pores.

3. The dressing of claim 1, wherein the collagen is a collagen film.

4. The dressing of claim 1, wherein the collagen is a collagen film having perforations.

5. The dressing of claim 1, wherein the contact layer comprises a film having fenestrations.

6. The dressing of claim 1, wherein the contact layer comprises at least two layers of collagen.

7. The dressing of claim 1, further comprising a glycerol coating disposed on the manifold, between the first side of the manifold and the contact layer and between the perimeter side of the manifold and the contact layer.

8. The dressing of claim 1, wherein the manifold comprises:

a center portion having a center hole of the plurality of through-holes;

a first perimeter portion concentric with the center portion;

a second perimeter portion concentric with the first perimeter portion; and a plurality of segments joining the center portion to the first perimeter portion and the first perimeter portion to the second perimeter portion, the plurality of segments forming concentric rings having peripheral holes of the plurality of through-holes.

9. The dressing of claim 8, further comprising a plurality of apertures disposed in the base layer, the plurality of apertures having a shape different than a shape of the peripheral holes.

10. The dressing of claim 1, wherein the contact layer covers the plurality of through-holes.

11. The dressing of claim 1, wherein the plurality of through-holes are configured to collapse laterally.

* * * * *